United States Patent
Nakayama et al.

(10) Patent No.: US 10,816,501 B2
(45) Date of Patent: Oct. 27, 2020

(54) GAS SENSOR AND METHOD FOR MANUFACTURING GAS SENSOR

(71) Applicant: NGK INSULATORS, LTD., Nagoya-shi, Aichi (JP)

(72) Inventors: Yuki Nakayama, Nagoya (JP); Noriko Hirata, Nagoya (JP); Taku Okamoto, Nagoya (JP); Osamu Nakasone, Inabe (JP)

(73) Assignee: NGK INSULATORS, LTD., Nagoya (JP)

(*) Notice: Subject to any disclaimer, the term of this patent is extended or adjusted under 35 U.S.C. 154(b) by 336 days.

(21) Appl. No.: 15/347,086

(22) Filed: Nov. 9, 2016

(65) Prior Publication Data

US 2017/0138893 A1    May 18, 2017

(30) Foreign Application Priority Data

Nov. 17, 2015   (JP) .................................. 2015-224643

(51) Int. Cl.
  *G01N 27/407*   (2006.01)
  *G01N 33/00*    (2006.01)
  *G01N 27/30*    (2006.01)

(52) U.S. Cl.
  CPC ....... *G01N 27/4075* (2013.01); *G01N 27/301* (2013.01); *G01N 27/4074* (2013.01); *G01N 33/0047* (2013.01)

(58) Field of Classification Search
  None
  See application file for complete search history.

(56) References Cited

U.S. PATENT DOCUMENTS

| | | | |
|---|---|---|---|
| 6,153,072 A | 11/2000 | Inoue et al. | |
| 8,133,370 B2 | 3/2012 | Roessler et al. | |
| 8,366,893 B2 | 2/2013 | Fujisaki et al. | |
| 2002/0023838 A1* | 2/2002 | Schneider | G01N 27/4071 204/429 |
| 2003/0205078 A1* | 11/2003 | Hasei | G01N 27/4074 73/23.31 |

FOREIGN PATENT DOCUMENTS

| | | |
|---|---|---|
| JP | 3566089 B2 | 6/2004 |
| JP | 4405643 B2 | 11/2009 |
| JP | 4914447 B2 | 1/2012 |
| JP | 5323752 B2 | 7/2013 |

* cited by examiner

*Primary Examiner* — Gurpreet Kaur
*Assistant Examiner* — Steven E Rosenwald
(74) *Attorney, Agent, or Firm* — Global IP Counselors, LLP

(57) ABSTRACT

A gas sensor with excellent detection sensitivity is provided. A sensing electrode, which is provided in a mixed-potential gas sensor for measuring a concentration of a predetermined gas component of a measurement gas to sense the predetermined gas component, is formed of a cermet of a noble metal and an oxygen-ion conductive solid electrolyte. The noble metal includes Pt and Au. A range of at least 1.5 nm from a surface of a noble metal particle included in the sensing electrode is a Au enriched region having a Au concentration of 10% or more.

20 Claims, 8 Drawing Sheets

GAS SENSOR AND METHOD FOR MANUFACTURING GAS SENSOR

BACKGROUND OF THE INVENTION

Field of the Invention

The present invention relates to a gas sensor for sensing a predetermined gas component of a measurement gas, and more particularly, to a sensing electrode of the gas sensor.

Description of the Background Art

Gas sensors that sense a predetermined gas component of a measurement gas to determine its concentration come in various types such as a semiconductor gas sensor, a catalytic combustion gas sensor, an oxygen-concentration difference sensing gas sensor, a limiting current gas sensor, and a mixed-potential gas sensor (for example, see Japanese Patent Nos. 3566089, 4405643, 4914447, and 5323752). Some of these gas sensors are obtained by providing electrodes containing a noble metal as its main constituent to a sensor element mainly made of ceramic that is a solid electrolyte such as zirconia.

Japanese Patent Nos. 3566089 and 5323752 each disclose a limiting current gas sensor including a sensor element formed of solid electrolyte, which includes electrodes made of Pt—Au alloy as pumping electrodes.

Japanese Patent No. 4405643 discloses a gas sensor including a thin layer mainly made of Pt or Au to compensate for the adhesion between a solid electrolyte and an electrode made of a metal oxide and gold.

Japanese Patent No. 4914447 discloses a mixed-potential gas sensor including a first electrode formed through application of a Pt—Au paste and a second electrode formed through application of a Pt paste and Au plating.

In response to more stringent regulations on exhaust gases, there have recently been increasing demands for a diagnosis of failure in the performance of cleaning unburned hydrocarbon in an exhaust emission control system (TWC: three-way catalyst) of a gasoline engine and a diagnosis of failure in the performance of cleaning unburned hydrocarbon in an exhaust emission control system (DOC: diesel oxidation catalyst) of a diesel engine. These diagnoses require a gas sensor capable of sensing an unburned hydrocarbon gas and identifying its concentration.

The inventors of the present invention have made intensive studies to find out that in a sensing electrode made of Pt—Au alloy having an increased Au abundance ratio near the surface of a particle of the electrode, a catalytic activity against a hydrocarbon gas is disabled, inducing a mixed potential having correlation with the concentration of the hydrocarbon gas. Such finding has led the inventors to a gas sensor capable of sensing a hydrocarbon gas with high sensitivity.

In the invention disclosed in Japanese Patent No. 4914447, the concentration of a gas component is determined on the premise that both of the first electrode and the second electrode have a catalytic activity, although there may be a slight difference. In Japanese Patent No. 4405643, the relationship between the alloy composition and the detection sensitivity of the electrode is not clear.

Japanese Patent No. 5323752 discloses that a pumping electrode for a limiting current gas sensor is made of Pt—Au alloy such that a Au abundance ratio on the surface of a particle of the electrode is 0.01 or more and 0.3 or less, thereby increasing the selective decomposition ability for oxygen in the pumping electrode. Japanese Patent No. 5323752 also discloses that a Au abundance ratio exceeding 0.3 is not preferable because such a ratio increases electrode impedance. Japanese Patent No. 5323752, however, discloses or suggests nothing about a mixed-potential gas sensor (needless to say, about its sensing electrode as well).

SUMMARY OF THE INVENTION

The present invention relates to a gas sensor for sensing a predetermined gas component of a measurement gas, and more particularly, is directed to a sensing electrode of a mixed-potential gas sensor.

According to the present invention, a mixed-potential gas sensor for measuring a concentration of a predetermined gas component of a measurement gas includes a sensor element mainly made of an oxygen-ion conductive solid electrolyte, a sensing electrode located on a surface of the sensor element, and a reference electrode including a cermet of Pt and an oxygen-ion conductive solid electrolyte. The sensing electrode includes a cermet of a noble metal and an oxygen-ion conductive solid electrolyte. The noble metal includes Pt and Au. A range of at least 1.5 nm from a surface of a noble metal particle included in the sensing electrode is a Au enriched region having a Au concentration of 10% or more. The gas sensor determines the concentration of the predetermined gas component based on a potential difference between the sensing electrode and the reference electrode.

According to the present invention, a method for manufacturing the gas sensor includes the steps of: preparing a plurality of green sheets each including the solid electrolyte; applying a conductive paste whose weight ratio of Au to a noble metal component is 10 wt % or more to one of the plurality of green sheets to form a pattern of the sensing electrode; forming a laminated body of the plurality of green sheets including the green sheet on which the pattern of the sensing electrode has been formed; and firing the laminated body to integrally fire the sensing electrode with the solid electrolyte. A Au vapor pressure near the pattern of the sensing electrode is set to $10^{-6}$ atm or more when the laminated body is fired.

According to the present invention, a gas sensor with excellent durability is achieved, which has excellent initial detection characteristics and in which temporal decrease in output is prevented or reduced.

The present invention therefore has an object to provide a gas sensor having excellent detection sensitivity.

DESCRIPTION OF THE PREFERRED EMBODIMENTS

First Configuration

Figure 1A:
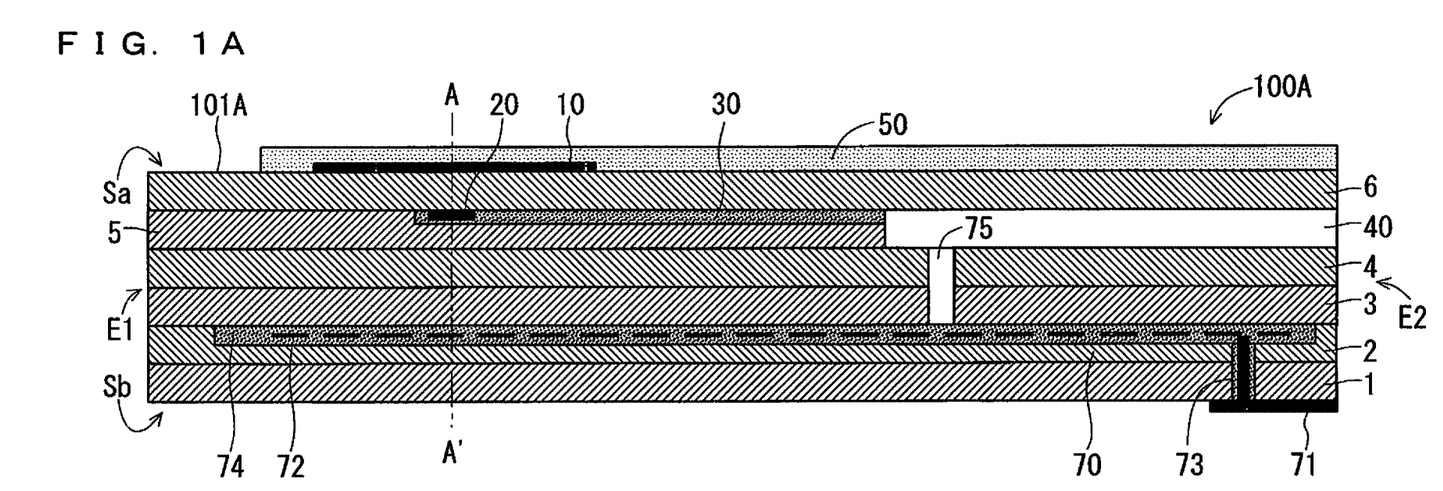
FIGS. 1A and 1B are sectional views schematically illustrating an example configuration of a gas sensor 100A according to a first configuration.
Figure 1B:
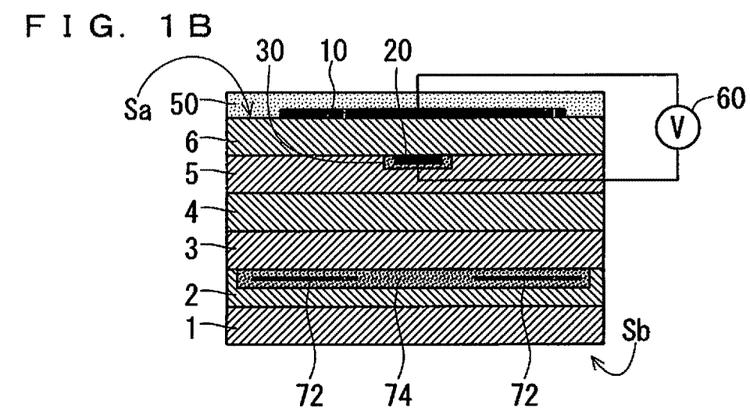

FIGS. 1A and 1B are schematic sectional views schematically illustrating an example configuration of a gas sensor 100A according to a first configuration of the present invention. FIG. 1A is a vertical sectional view of a sensor element 101A, which is a main component of the gas sensor 100A, taken along the longitudinal direction of the sensor element 101A. FIG. 1B is a view including a cross-section of the sensor element 101A perpendicular to the longitudinal direction of the sensor element 101A at a position A-A' of FIG. 1A.

The gas sensor 100A according to the first configuration of the present invention is a so-called mixed-potential gas sensor. Generally speaking, the gas sensor 100A determines the concentration of a gas component, which is a measurement target, of a measurement gas using a potential difference that occurs between a sensing electrode 10, which is provided on the surface of the sensor element 101A mainly made of ceramic that is an oxygen-ion conductive solid electrolyte such as zirconia ($ZrO_2$), and a reference electrode 20, which is provided inside the sensor element 101A, due to a difference in the concentration of the gas component between the portions near the electrodes based on the principle of mixed potential.

More specifically, the gas sensor 100A preferably determines the concentration of a predetermined gas component of a measurement gas, where the measurement gas is an exhaust gas present in an exhaust pipe of an internal combustion engine such as a diesel engine or a gasoline engine. In this specification, description will be given of an example case where a predetermined gas component being a measurement target is an unburned hydrocarbon gas. In such a case, examples of the unburned hydrocarbon gas include carbon monoxide (CO) in addition to typical hydrocarbon gases (gases classified as hydrocarbons in terms of chemical formula) such as $C_2H_4$, $C_3H_6$, and n-C8. In the presence of a plurality of unburned hydrocarbon gases in a measurement gas, a potential difference occurring between the sensing electrode 10 and the reference electrode 20 is a value reflecting all the plurality of unburned hydrocarbon gases, and thus, a concentration value to be determined is also a total sum of the concentrations of the plurality of unburned hydrocarbon gases.

The sensor element 101A mainly includes a reference gas introduction layer 30, a reference gas introduction space 40, and a surface protective layer 50 in addition to the sensing electrode 10 and the reference electrode 20 described above.

In the first configuration of the present invention, the sensor element 101A has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A and 1B. The sensor element 101A additionally includes other components mainly between these layers or on an outer peripheral surface of the element. The solid electrolytes constituting these six layers are fully airtight. Such a sensor element 101A is manufactured by, for example, laminating ceramic green sheets corresponding to the individual layers, which have been subjected to a predetermined process and printing of a circuit pattern, and further, by integrating the laminated layers through firing.

The gas sensor 100A does not necessarily need to include the sensor element 101A formed of such a laminated body including the six layers. The sensor element 101A may be formed as a laminated body having more or fewer layers or may not have a laminated structure.

In the following description, for convenience' sake, the surface located as the upper surface of the sixth solid electrolyte layer 6 in FIGS. 1A and 1B is referred to as a front surface Sa of the sensor element 101A, and the surface located as the lower surface of the first solid electrolyte layer 1 in FIGS. 1A and 1B is referred to as a rear surface Sb of the sensor element 101A. In the determination of the concentration of the unburned hydrocarbon gas in a measurement gas with the gas sensor 100A, a predetermined range starting from a distal end E1 being one end of the sensor element 101A, which includes at least the sensing electrode 10, is disposed in a measurement gas atmosphere; the other portion including a base end E2 opposite to the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view at a position closer to the distal end E1 that is one end in the longitudinal direction of the sensor element 101A on the front surface Sa of the sensor element 101A. The gas sensor 100A is placed such that, in its use, the sensor element 101A corresponding to at least the portion in which the sensing electrode 10 is provided is exposed to a measurement gas.

The catalytic activity of the sensing electrode 10 against an unburned hydrocarbon gas is disabled by preferably determining the composition of the Pt—Au alloy being its constituent material. That is, the decomposition reaction of an unburned hydrocarbon gas is prevented or reduced in the sensing electrode 10. In the gas sensor 100A, accordingly, the potential of the sensing electrode 10 selectively varies with respect to (has correlation with) the unburned hydrocarbon gas, in accordance with its concentration. In other words, the sensing electrode 10 is provided so as to have high dependence of potential on concentration for an unburned hydrocarbon gas while having low dependence of potential on concentration for other components of the measurement gas.

More specifically, in the sensor element 101A of the gas sensor 100A according to the first configuration of the present invention, the sensing electrode 10 is provided so as to have a preferably determined Au concentration in the surface of the Pt—Au alloy particle included in the sensing electrode 10, thereby exhibiting a strong dependence of potential on concentration in a concentration range of at least 2000 ppmC or less. This means that the sensing electrode 10 is provided to preferably determine the concentration of an unburned hydrocarbon gas in a concentration range of 2000 ppmC or less.

In the gas sensor 100A, a predetermined range in a depth direction (grain size direction) from the surface of the Pt—Au alloy particle included in the sensing electrode 10 is a Au enriched region having a high Au concentration. This prevents or reduces the degradation of the sensing electrode 10 associated with the Au desorption from the sensing electrode 10, resulting in the gas sensor 100A in which a temporal decrease in output is prevented or reduced and which has long-lasting stability (durability).

In this specification, the Au concentration basically means an area ratio of the portion covered with Au to the surface of a noble metal particle included in the sensing electrode 10. In this specification, a Au concentration is calculated from an expression below $$\text{Au concentration (\%)}=100\times\text{Au detection value}/(\text{Au detection value}+\text{Pt detection value}) \quad (1)$$

where Au and Pt detection values are values in an Auger spectrum obtained by performing a measurement on the surface of the noble metal particle by Auger electron spectroscopy (AES). In this specification, a value, which is obtained by the calculation based on Expression (1) using the Au detection value and the Pt detection value obtained by AES depth profile analysis of the noble metal particle included in the sensing electrode 10, is also regarded as a Au concentration at a relevant depth position (assuming that the depth position is in the surface of the particle).

If the sensing electrode 10 is exposed due to the lack of a surface protective layer 50, which will be described below, AES measurement may be performed on the noble metal particle present on the surface of the sensing electrode 10. If the sensing electrode 10 is not exposed, AES measurement may be performed on the surface of the noble metal particle present on a cutout surface of the sensing electrode 10, which is obtained by cutting out the sensor element 101A at a position corresponding to the sensing electrode 10.

The Au enriched region is a region having a Au concentration of 10% or more, which is calculated from Expression (1).

The sensing electrode 10 will be described below in detail.

The reference electrode 20 is an electrode having a substantially rectangular shape in plan view, which is provided inside the sensor element 101A and serves as a reference in the determination of the concentration of the measurement gas. The reference electrode 20 is provided as a porous cermet electrode of Pt and zirconia.

It suffices that the reference electrode 20 has a porosity of 10% or more and 30% or less and a thickness of 5 μm or more and 15 μm or less. The plane size of the reference electrode 20 may be smaller than that of the sensing electrode 10 as illustrated in FIGS. 1A and 1B, or may be equal to that of the sensing electrode 10 as in a second configuration, which will be described below (see FIGS. 3A and 3B).

The reference gas introduction layer 30 is a layer made of porous alumina, which is provided inside the sensor element 101A to cover the reference electrode 20. The reference gas introduction space 40 is an internal space provided near the base end E2 of the sensor element 101A. Air (oxygen), serving as a reference gas in the determination of the concentration of an unburned hydrocarbon gas, is externally introduced into the reference gas introduction space 40.

The reference gas introduction space 40 and the reference gas introduction layer 30 are in communication with each other, and accordingly, in the use of the gas sensor 100A, the surrounding of the reference electrode 20 is always filled with air (oxygen) through the reference gas introduction space 40 and the reference gas introduction layer 30. During the use of the gas sensor 100A, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even when the sensing electrode 10 is exposed to the measurement gas.

In the case illustrated in FIG. 1A, the reference gas introduction space 40 is provided in such a manner that part of the fifth solid electrolyte layer 5 is in communication with the exterior on the base end E2 of the sensor element 101A. The reference gas introduction layer 30 is provided so as to extend in the longitudinal direction of the sensor element 101A between the fifth solid electrolyte layer 5 and the sixth solid electrolyte layer 6. The reference electrode 20 is provided under the center of gravity of the sensing electrode 10 with reference to FIGS. 1A and 1B.

The surface protective layer 50 is a porous layer made of alumina, which is provided so as to cover at least the sensing electrode 10 on the front surface Sa of the sensor element 101A. The surface protective layer 50 is provided as an electrode protective layer that prevents or reduces the degradation of the sensing electrode 10 due to continuous exposure to a measurement gas during the use of the gas sensor 100A. In the case illustrated in FIG. 1A, the surface protective layer 50 is provided so as to cover not only the sensing electrode 10 but also substantially the entire front surface Sa of the sensor element 101A except for a predetermined range starting from the distal end E1.

As illustrated in FIG. 1B, the gas sensor 100A is equipped with a potentiometer 60 capable of measuring a potential difference between the sensing electrode 10 and the reference electrode 20. Although FIG. 1B schematically illustrates wiring of the sensing electrode 10, the reference electrode 20, and the potentiometer 60, in an actual sensor element 101A, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The sensing electrode 10 and the reference electrode 20 are electrically connected with the potentiometer 60 through the wiring patterns and the connection terminals. Hereinbelow, a potential difference between the sensing electrode 10 and the reference electrode 20, which is measured by the potentiometer 60, is also referred to as a sensor output.

The sensor element 101A further includes a heater part 70, which performs temperature control of heating the sensor element 101A and maintaining the temperature of the sensor element 101A, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101A (in FIGS. 1A and 1B, the lower surface of the first solid electrolyte layer 1). The heater part 70 can be powered externally by the heater electrode 71 connected with an external power supply (not shown).

The heater 72 is an electric resistor provided inside the sensor element 101A. The heater 72 is connected with the heater electrode 71 through the through hole 73 and generates heat by being powered externally via the heater electrode 71 to heat the solid electrolytes forming the sensor element 101A and maintain their temperatures.

In the case illustrated in FIGS. 1A and 1B, the heater 72 is buried while being vertically sandwiched between the second solid electrolyte layer 2 and the third solid electrolyte layer 3 so as to extend from the base end E2 to the position below the sensing electrode 10 near the distal end E1. This enables the adjustment of the entire sensor element 101A to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth solid electrolyte layer 4 and to be in communication with the reference gas introduction space 40, and is formed to mitigate an internal pressure rise associated with a temperature rise in the heater insulating layer 74.

In the determination of the concentration of an unburned hydrocarbon gas in a measurement gas using the gas sensor 100A having such a configuration, as described above, air (oxygen) is supplied to the reference gas introduction space 40, with the sensor element 101A in only a predetermined range, which starts from the distal end E1 and includes at least the sensing electrode 10, being disposed in a space containing a measurement gas, and with the sensor element 101A on the base end E2 being apart from the space. The heater 72 heats the sensor element 101A to an appropriate temperature from 400° C. to 800° C., preferably from 500° C. to 700° C., more preferably from 500° C. to 600° C.

In such a state, a potential difference occurs between the sensing electrode 10 exposed to the measurement gas and the reference electrode 20 exposed to the air. As described above, however, the potential of the reference electrode 20 disposed in the air (having a constant oxygen concentration) atmosphere is maintained at a constant potential, whereas the potential of the sensing electrode 10 selectively has a dependence on concentration for the unburned hydrocarbon gas of the measurement gas. The potential difference (sensor output) is thus substantially a value according to the composition of the measurement gas present around the sensing electrode 10. Therefore, a certain functional relationship (referred to as sensitivity characteristics) holds between the concentration of the unburned hydrocarbon gas and the sensor output. In the description below, such sensitivity characteristics may also be referred to as, for example, sensitivity characteristics for the sensing electrode 10.

In the actual determination of the concentration of an unburned hydrocarbon gas, in advance, a plurality of different mixed gases, each of which has a known concentration of an unburned hydrocarbon gas, are used as the measurement gas, and the sensitivity characteristics are experimentally identified by performing a measurement on the sensor output for each measurement gas. In the actual use of the gas sensor 100A, accordingly, an operation processor (not shown) converts the sensor output, which varies from moment to moment in accordance with the concentration of an unburned hydrocarbon gas in a measurement gas, into the concentration of the unburned hydrocarbon gas based on the sensitivity characteristics. The concentration of the unburned hydrocarbon gas in the measurement gas can thus be determined almost in real time.

Modification of First Configuration

Figure 2A:
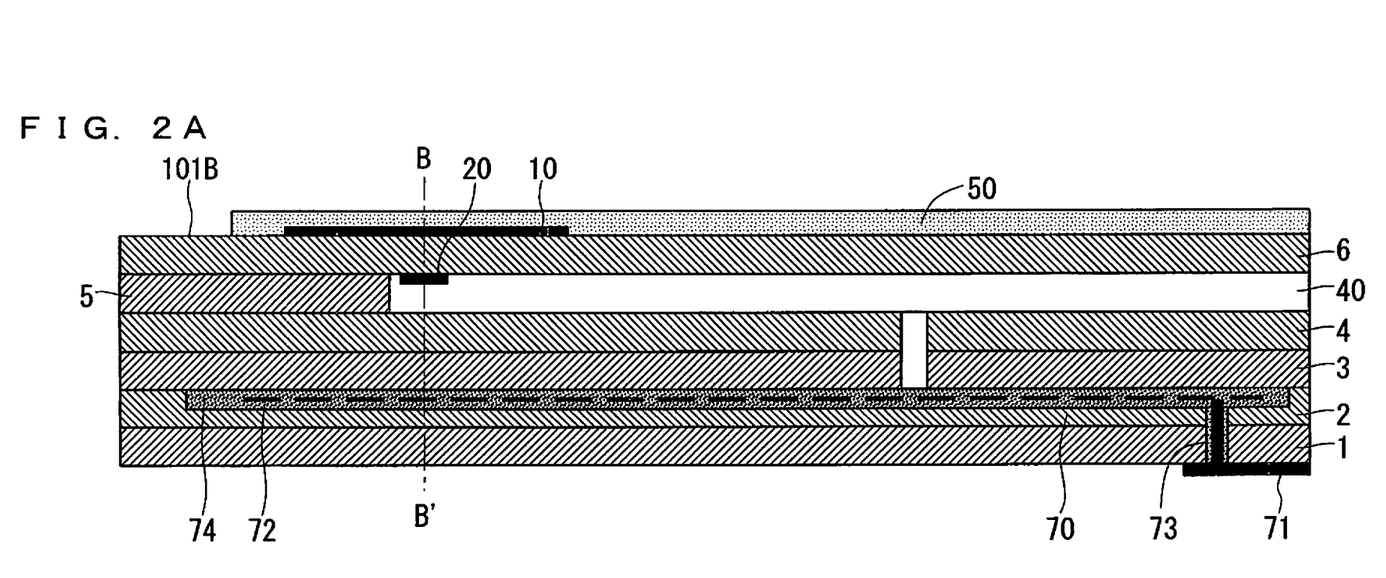
FIGS. 2A and 2B are sectional views schematically illustrating an example configuration of a gas sensor 100B that is a modification of the gas sensor 100A.
Figure 2B:
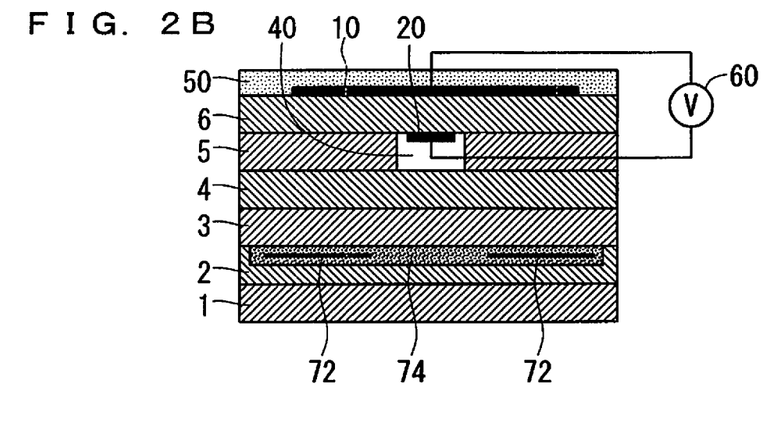

FIGS. 2A and 2B are schematic sectional views schematically illustrating an example configuration of a gas sensor 100B, which is a modification of the gas sensor 100A. FIG. 2A is a vertical sectional view of a sensor element 101B, which is a main component of the sensor element 101B, taken along the longitudinal direction of the gas sensor 100B. FIG. 2B is a view including a cross-section of the sensor element 101B perpendicular to the longitudinal direction of the sensor element 101B at a position B-B' of FIG. 2A.

The gas sensor 100B is provided in such a manner that the reference gas introduction space 40 of the sensor element 101A of the gas sensor 100A is extended to below the sensing electrode 10, whereas the reference gas introduction layer 30 is omitted and the reference electrode 20 is exposed to the reference gas introduction space 40. The other configurational elements are similar to those of the gas sensor 100A. Thus, the way how a sensor output occurs and a Au enriched region is formed in the sensing electrode 10 is the same as in the case of the gas sensor 100A. In other words, similarly to the gas sensor 100A, the gas sensor 100B is a so-called mixed-potential gas sensor, in which the degradation of the sensing electrode 10 is prevented or reduced.

The gas sensor 100B having the configuration as described above, which includes the sensor element 101B and has sensitivity characteristics determined in advance similarly to the gas sensor 100A, can determine the concentration of an unburned hydrocarbon gas in a measurement gas. In the gas sensor 100B, a temporal decrease in output is prevented or reduced, and long-lasting stability (durability) is achieved.

Second Configuration

Figure 3A:
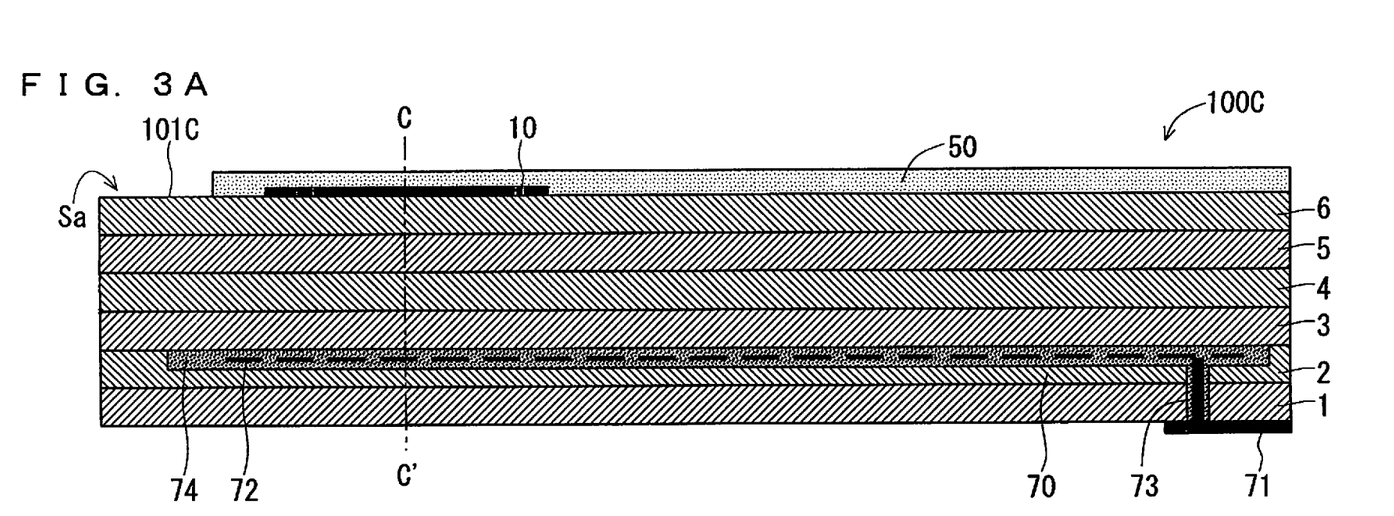
FIGS. 3A and 3B are sectional views schematically illustrating an example configuration of a gas sensor 100C according to a second configuration.
Figure 3B:
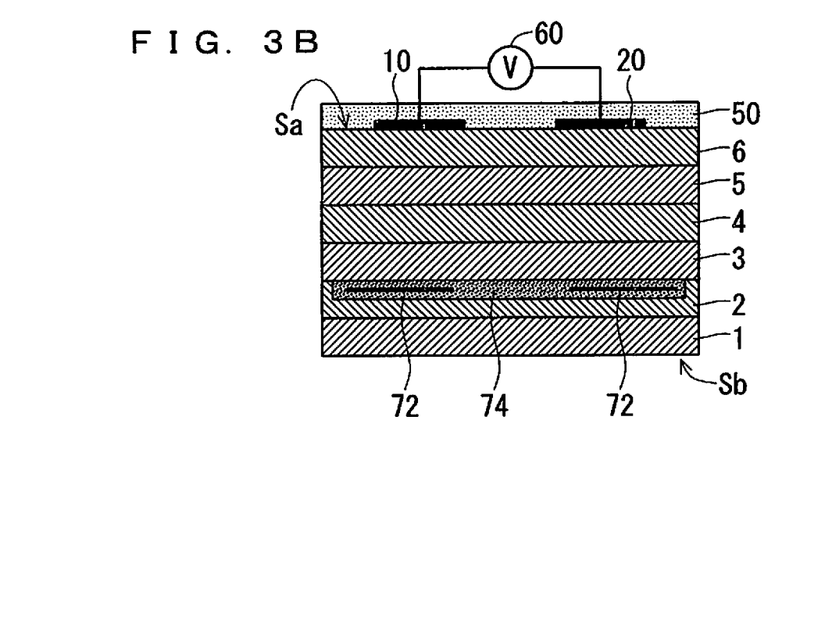

FIGS. 3A and 3B are schematic sectional views schematically illustrating a configuration example of a gas sensor 100C according to a second configuration of the present invention. FIG. 3A is a vertical sectional view of a sensor element 101C, which is a main component of the gas sensor 100C, taken along the longitudinal direction of the sensor element 101C. FIG. 3B is a view including a cross-section of the sensor element 101C perpendicular to the longitudinal direction of the sensor element 101C at a position C-C' of FIG. 3A.

The gas sensor 100C is also a so-called mixed-potential gas sensor similarly to the gas sensors 100A and 100B. In the sensor element 101C of the gas sensor 100C, however, not only the sensing electrode 10 but also the reference electrode 20 is disposed on the front surface Sa of the sensor element 101C and is covered with the surface protective layer 50, differently from the sensor element 101A and the sensor element 101B. The constituent materials for the respective electrodes of the gas sensor 100C are the same as those of the gas sensors 100A and 100B.

The gas sensor 100C includes no reference gas introduction space 40 (further, no reference gas introduction layer 30) and no pressure diffusion hole 75. The other components of the gas sensor 100C are similar to those of the gas sensors 100A and 100B. Although the sensing electrode 10 and the reference electrode 20 are provided at the same position in the longitudinal direction of the gas sensor 100C (see FIG. 3B) in the case illustrated in FIGS. 3A and 3B, these electrodes may be disposed at different positions, for example, may be disposed in the longitudinal direction of the sensor element 101C.

In the determination of the concentration of an unburned hydrocarbon gas in a measurement gas using the gas sensor 100C having such a configuration, the sensor element 101C is disposed in such a manner that the reference electrode 20 as well as the sensing electrode 10 is exposed to the measurement gas, unlike the gas sensors 100A and 100B. Although the sensing electrode 10 and the reference electrode 20 are accordingly exposed to the same atmosphere, the constituent materials for the respective electrodes are the same as those for the gas sensors 100A and 100B. In the gas sensor 100C, thus, the potential of the sensing electrode 10 varies selectively with respect to the concentration of an unburned hydrocarbon gas as in the gas sensors 100A and 100B. Unlike the sensing electrode 10, the catalytic activity of the reference electrode 20, which is formed as a porous cermet electrode of Pt and zirconia, is not prevented or reduced against a specific gas component. As a result, the sensing electrode 10 and the reference electrode 20 are identical in behavior toward gas components other than the unburned hydrocarbon gas. Thus, the sensor output of the gas sensor 100C substantially varies in accordance with an unburned hydrocarbon gas present in a measurement gas.

Also in the gas sensor 100C, as in the gas sensors 100A and 100B, the sensing electrode 10 is formed so as to include a Au enriched region, so that the degradation of the sensing electrode 10 is prevented or reduced.

Similarly to the gas sensors 100A and 100B, thus, the gas sensor 100C whose sensitivity characteristics have been identified in advance can determine the concentration of an unburned hydrocarbon gas in a measurement gas. Thus, in the gas sensor 100C, a temporal decrease in output is prevented or reduced, and long-lasting stability (durability) is achieved.

Outline of Process of Manufacturing Sensor Element

Next, the process of manufacturing the sensor elements 101A to 101C will be described using an example case where these sensor elements have the layer structures as illustrated in FIGS. 1A, 1B, 2A, 2B, 3A, and 3B. Generally speaking, the sensor elements 101A to 101C as illustrated in FIGS. 1A, 1B, 2A, 2B, 3A, and 3B are each manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

Figure 4:
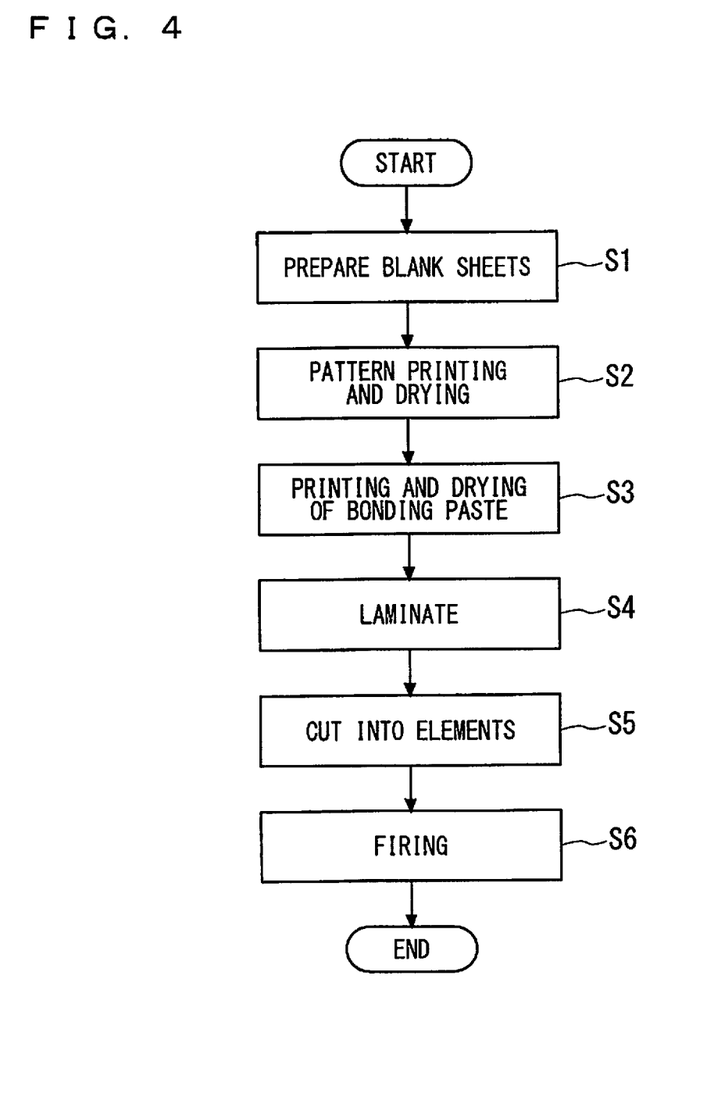
FIG. 4 is a flowchart illustrating a process of manufacturing the sensor elements 101A to 101C.

FIG. 4 is a flowchart illustrating the process of manufacturing the sensor elements 101A to 101C. In the manufacture of the sensor elements 101A to 101C, first, blank sheets (not shown) that are green sheets having no pattern formed thereon are prepared (step S1). Specifically, six blank sheets corresponding to the first to sixth solid electrolyte layers 1 to 6 are prepared. A blank sheet for forming the surface protective layer 50 is prepared as well. A plurality of sheet holes used for positioning in printing and lamination are provided in the blank sheets. Such sheet holes are formed in advance through, for example, punching by a punching machine. For a green sheet whose corresponding layer forms an internal space, a penetration corresponding to the internal space is also provided in advance through, for example, punching as described above. All the blank sheets corresponding to the respective layers of the sensor elements 101A to 101C need not to have the same thickness.

After the preparation of the blank sheets corresponding to the respective layers, pattern printing and drying are performed to form various patterns on the individual blank sheets (step S2). Specifically, electrode patterns of, for example, the sensing electrode 10 and the reference electrode 20, the reference gas introduction layer 30, internal wiring (not shown), and the like are formed. In the first solid electrolyte layer 1, a cut mark is printed that serves as a reference cut position when the laminated body is cut in a subsequent step.

Each pattern is printed by applying a paste for pattern formation, prepared in accordance with the characteristic required for each formation target, to the blank sheet by a known screen printing technique. Any known drying means is available for drying after printing.

After the pattern printing, printing and drying of a bonding paste are performed to laminate and bond the green sheets corresponding to the respective layers (step S3). Any known screen printing technique is available for printing of a bonding paste, and any known drying means is available for drying after printing.

Subsequently, crimping is performed in which the adhesive-applied green sheets are laminated in a predetermined order, and the laminated green sheets are crimped on the predetermined temperature and pressure conditions, to thereby form a laminated body (step S4). Specifically, green sheets that are lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body has been obtained as described above, subsequently, a plurality of parts of the laminated body are cut out as individual units (referred to as element bodies) of the sensor elements 101A to 101C (step S5). The cut out element bodies are fired under predetermined conditions, thereby producing the sensor elements 101A to 101C as described above (step S6). In other words, the sensor elements 101A to 101C are produced by integrally firing the solid electrolyte layers and the electrodes. The firing temperature is preferably 1200° C. or higher and 1500° C. or lower. The integral firing performed in such a manner provides satisfactory adhesion strength to the respective electrodes of the sensor elements 101A to 101C.

The resultant sensor elements 101A to 101C are housed in a predetermined housing and incorporated into main bodies (not shown) of the gas sensors 100A to 100C.

Details of Sensing Electrode

Figure 5A:
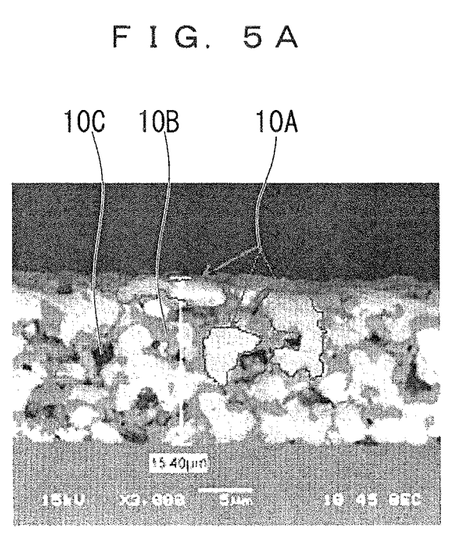
FIGS. 5A and 5B illustrate scanning electron microscope (SEM) images of a sensing electrode 10.
Figure 5B:
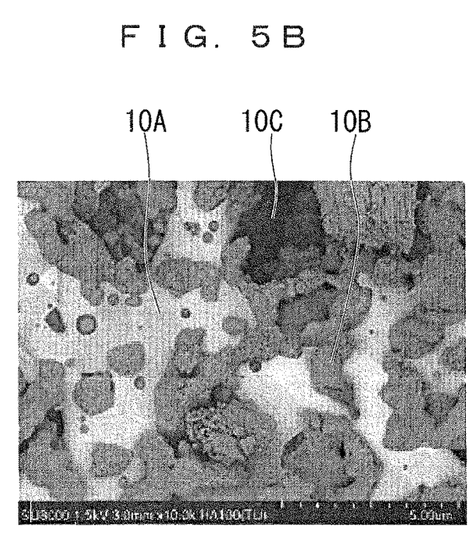
Figure 6A:
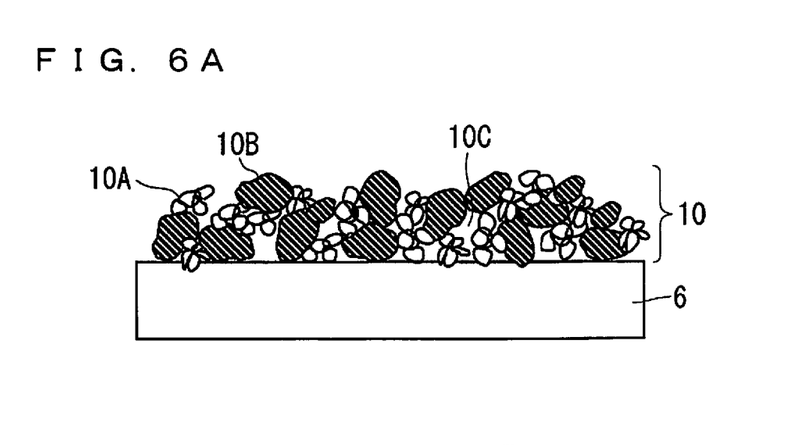
FIGS. 6A, 6B, and 6C schematically illustrate a detailed configuration of the sensing electrode 10.
Figure 6B:
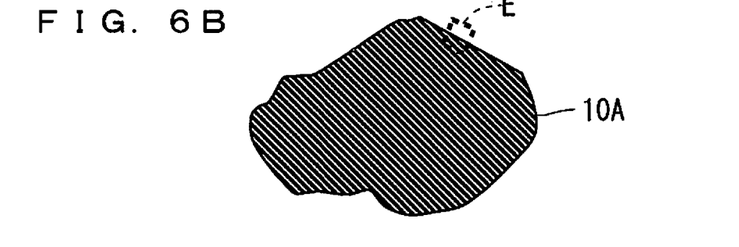
Figure 6C:
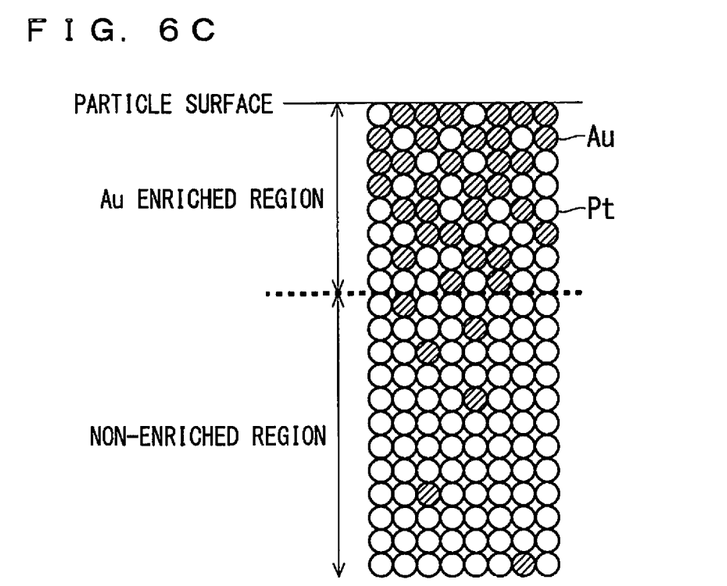

FIGS. 5A and 5B illustrate scanning electron microscope (SEM) images of the sensing electrode 10. FIGS. 5A and 5B illustrate an image of a cross-section and an image of a surface, respectively, of the sensing electrode 10. FIGS. 6A, 6B, and 6C schematically illustrate a detailed configuration of the sensing electrode 10. As described above, the sensing electrode 10 is formed as a porous cermet electrode. More specifically, as illustrated in FIGS. 5A and 5B, further, as schematically illustrated in FIG. 6A, such a formation is achieved by the presence of a large number of Pt—Au alloy particles 10A (observed as white portions in FIGS. 5A and 5B) and a large number of zirconia (YSZ) particles 10B (observed as gray portions in FIGS. 5A and 5B) randomly adjacent to one another with holes 10C (observed as black portions in FIGS. 5A and 5B) formed at places in a predetermined range on the sixth solid electrolyte layer 6.

In the gas sensors 100A to 100C, as described above, the sensing electrode 10 is formed in such a manner that the catalytic activity against an unburned hydrocarbon gas is disabled and that a predetermined range near the surface of the Pt—Au alloy particle included in the sensing electrode 10 is the Au enriched region. FIG. 6B is an enlarged view of the Pt—Au alloy particle 10A included in the sensing electrode 10 illustrated in FIG. 6A. FIG. 6C schematically illustrates an atomic arrangement at a part E near the surface of the Pt—Au alloy particle 10A. As illustrated in FIG. 6C, the Au enriched region near the surface of the Pt—Au alloy particle 10A is formed as a region with a higher abundance ratio of Au atoms than a non-enriched region remote from the particle surface.

Specifically, the sensing electrode 10 is formed in such a manner that a range of at least 1.5 nm in depth from the surface of the Pt—Au alloy particle 10A included in the sensing electrode 10 is a Au enriched region. In such a case, an effect that detection sensitivity becomes higher than in the case where no Au enriched region is formed is achieved, and besides, an effect that temporal variations in output (decrease in output) of the gas sensors 100A to 100C are prevented or reduced is achieved.

The former effect is due to a fact that the more an abundance ratio of Au having no catalytic activity against an unburned hydrocarbon gas is increased in the surface of the Pt—Au alloy particle 10A, compared with Pt having a catalytic activity against an unburned hydrocarbon gas (the more area ratio of Au in a particle surface is increased), the more likely to disable the catalytic activity of the sensing electrode 10 is, resulting in a higher potential of the sensing electrode 10.

The latter effect is due to a fact that, in the surface of the sensing electrode 10 including a Au enriched region also in the depth direction of the Pt—Au alloy particle 10A, a decrease in Au abundance ratio is prevented or reduced even when Au present in the surface of the Pt—Au alloy particle 10A desorbs from the surface during the continuous use of the gas sensors 100A to 100C.

The latter effect will be described more specifically. The sensor elements 101A to 101C respectively included in the gas sensors 100A to 100C are heated by the heater part 70 and receive heat also from the measurement gas atmosphere during their use. Consequently, the sensing electrode 10 is heated as well, and as a result of the heating, Au having a high saturated vapor pressure desorbs from the surface of the Pt—Au alloy particle 10A. If a Au enriched region is present only within a range of less than 1.5 nm in depth from the surface of the Pt—Au alloy particle 10A, the following problem occurs. At the beginning of the use of the gas sensors 100A to 100C, the catalytic activity of the sensing electrode 10 is disabled satisfactorily because of a high Au abundance ratio in the surface of the Pt—Au alloy particle 10A, and accordingly, a preferable sensor output is obtained; however, as the gas sensors 100A to 100C are continuously used, Au desorbs further from the surface of the Pt—Au alloy particle 10A to reduce a Au abundance ratio, resulting in a greatly reduced sensor output.

In the sensor elements 101A to 101C, the Au enriched region with high Au abundance ratio is present not only in the topmost surface but also in the depth direction of the Pt—Au alloy particle 10A included in the sensing electrode 10. This prevents or reduces a decrease in Au abundance ratio even when Au desorbs further from the surface of the Pt—Au alloy particle 10A. A temporal decrease in sensor output is thus also prevented or reduced.

The Au enriched region having such an operational advantage can be achieved by setting a Au charge amount in a paste for pattern formation (conductive paste), which is used to form the sensing electrode 10, to a predetermined value or more and by firing element bodies, which will turn into the sensor elements 101A to 101C, in an atmosphere of high Au vapor pressure. For example, at firing temperatures of 1300° C. to 1400° C., in theory, a sensing electrode 10 including a Au enriched region also in its depth direction is formed by adjusting firing conditions such that the atmosphere around the sensing electrode 10 is a Au-excess atmosphere in which a Au vapor pressure is $10^{-6}$ atm or more.

Figure 7A:
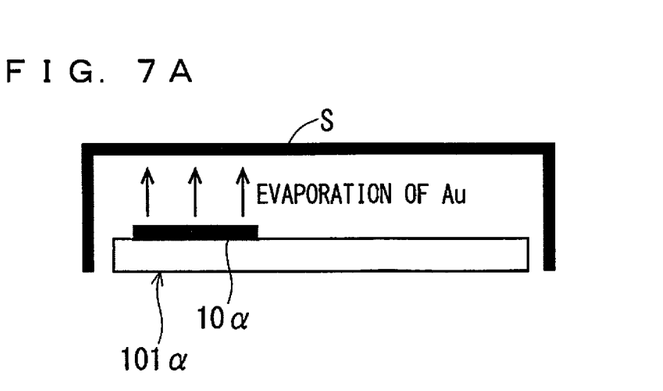
FIGS. 7A and 7B illustrate an example of a specific approach for setting a Au vapor pressure around the sensing electrode 10 to $10^{-16}$ atom or more.
Figure 7B:
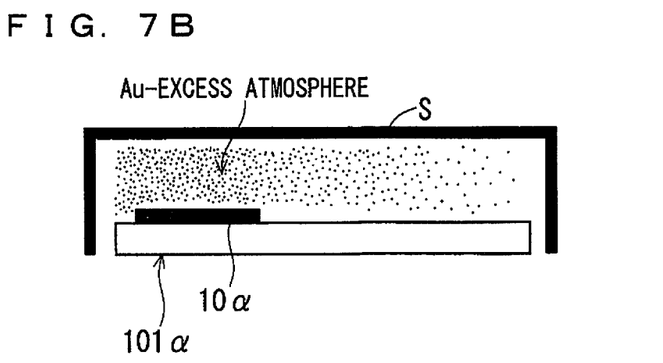

FIGS. 7A and 7B illustrate a specific approach for setting the Au vapor atmosphere around the sensing electrode 10 to $10^{-6}$ atm or more. In the case illustrated in FIGS. 7A and 7B, an element body 101a, which will turn into any of the sensor elements 101A to 101C through firing, placed inside a firing furnace (not shown) is enclosed (is covered with a predetermined clearance left) by an enclosure member such as a sheath member (cover member) S of dense alumina, so that the element body 101a is placed within a narrow space in relation to the internal volume of the firing furnace.

When the element body 101a is fired in such a state, as illustrated in FIG. 7A, Au evaporates (desorbs) during the firing from a paste film 10a, which will turn into a sensing electrode 10 through firing. However, the element body 101a is enclosed by the sheath member S, so that a Au-excess atmosphere as illustrated in FIG. 7B is achieved near the paste film 10a inside the sheath member S, even when a relatively small amount of Au atoms evaporate. Since Au is less likely to evaporate from the paste film 10a in the Au-excess atmosphere, during the formation of the sensing electrode 10 with the progress of firing of the paste film 10a, Au atoms in the paste film 10a come to be present locally in the front surface of the Pt—Au alloy particle 10A. Finally, a Au enriched region is formed.

The Au enriched region can be formed as described above by satisfying the relationship "the Au amount required to set the internal atmosphere of the sheath member to a Au equilibrium vapor pressure<<the Au amount in the paste film 10a" (the Au amount required to set the internal atmosphere of the sheath member to Au equilibrium vapor pressure is sufficiently smaller than the Au amount in the paste film 10a). Specific conditions in the formation, such as a Au mixing ratio in the paste film 10a, a size (internal volume) and a clearance distance from the element body 101a of the sheath member S, and firing conditions, can be determined appropriately while reflecting the sizes of the sensor elements 101A to 101C to be manufactured and the size of the sensing electrode 10.

If no sheath member S is provided, the relationship "the Au amount required to set the internal atmosphere of the firing furnace to a Au equilibrium vapor pressure>>the Au amount in the paste film 10a" (the Au amount required to set the internal atmosphere of the firing furnace to Au equilibrium vapor pressure is sufficiently larger than the Au amount in the paste film 10a) is satisfied, and accordingly, Au is not likely to be enriched sufficiently.

In setting the Au vapor pressure around the sensing electrode 10 to $10^{-6}$ atm or more, the paste film 10a may be covered with a low-porosity protective layer, in addition to placing the sheath member S as illustrated in FIGS. 7A and 7B.

The volume ratio of the noble metal component and zirconia in the sensing electrode 10 may be from approximately 4:6 to 8:2.

For the gas sensors 100A to 100C to preferably exhibit their functions, the porosity of the sensing electrode 10 is preferably 10% or more and 30% or less, and the thickness of the sensing electrode 10 is preferably 5 μm or more.

The plane size of the sensing electrode 10 may be appropriately determined, and it suffices that, for example, the length of the sensor element in the longitudinal direction is approximately 2 to 10 mm and the length of the sensor electrode 10 in the direction perpendicular to the longitudinal direction is approximately 1 to 5 mm.

Conductive Paste for Forming Sensing Electrode

Next, a conductive paste used to form the sensing electrode 10 will be described. The conductive paste for forming a sensing electrode is produced by using a Au ion-containing liquid as a Au starting material and mixing the Au ion-containing liquid with powdered Pt, powdered zirconia, and a binder. Any binder, which can disperse any other row material to the printable extent and vanishes through firing, may be appropriately selected. The production of a conductive paste in such a manner is referred to as liquid-state Au mixing.

Here, the Au ion-containing liquid is obtained by dissolving a salt containing a Au ion or an organometallic complex containing a Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the sensing electrodes 10 formed in the sensor elements 101A to 101C obtained through the above-mentioned manufacturing process contain Au mainly as an alloy with Pt.

In this embodiment, in the production of a conductive paste for forming a sensing electrode through liquid-state Au mixing, the ratio of a weight of Au to a weight of all noble metal elements (a sum of weights of Pt and Au) in a starting material is set to 10 wt % or more. In such a case, a Au enriched region can be formed in a range of at least 1.5 nm in depth from the surface of the Pt—Au alloy particle 10A by setting the Au vapor pressure around the sensing electrode 10 to $10^{-6}$ atm or more with the use of the sheath member S as described above during firing. In the case that a Au mixing ratio is set to 10 wt % and the sheath member S is used during firing, the Au concentration in the surface of the Pt—Au alloy particle 10A can be set to 20 to 30%.

In the formation of the sensing electrode 10 using a conductive paste produced through liquid-state Au mixing, the Au concentration in the surface of the Pt—Au alloy particle 10A may be increased with an increased Au mixing ratio, and a Au enriched region can be formed in a region deeper from the surface. However, Au particles are likely to agglomerate between the production and firing of the conductive paste, and accordingly, the sensing electrode 10 itself may not be formed preferably. In practice, the sensing electrode 10 functions preferably if the Au concentration in the surface of the Pt—Au alloy particle 10A is at least approximately 10%. Therefore, it is preferable from the viewpoint of stability to achieve a Au concentration of 10% or more in a range deeper from the surface of the Pt—Au alloy particle 10A rather than to achieve a Pt—Au alloy particle 10A having an extremely high (for example, greatly exceeding 30%) Au concentration only in the surface of the Pt—Au alloy particle 10A. Au concentrations of smaller than 9% in the surface of the Pt—Au alloy particle 10A are not preferable, because the catalytic activity of the sensing electrode 10 is not disabled, and the measurement gas burns through Pt catalytic action on the surface of the sensing electrode 10, so that no sensor output is obtained.

Another Way of Forming Sensing Electrode

The way of producing the sensing electrode 10 is not limited to the way using the conductive paste produced through liquid-state Au mixing as described above. For example, a conductive paste may be produced using coated powder, which is obtained by coating powdered Pt with Au, or a powdered Pt—Au alloy as a starting raw material, or a technique of forming a thin film electrode, such as sputtering, may be employed. Alternatively, a sensing electrode 10 may be formed by a secondary firing (two-stage firing) technique of performing printing and drying with a conductive paste for forming a sensing electrode after a sensor element has been obtained through firing without forming a sensing electrode 10, and further performing firing. Depending on a technique employed, a Pt—Au alloy particle 10A can be achieved that has a Au concentration greatly exceeding 30% on its surface and includes a Au enriched region formed in a range greatly exceeding 1.5 nm from its surface.

Modifications

Although the results of AES analysis are used to calculate Au concentrations in the embodiment above, a technique of calculating Au concentrations is not limited to this technique. Alternatively, analysis values obtained in any other analysis technique may be used. For example, the results of the analysis in a depth direction by secondary ion mass spectrometry (SIMS) may be used to calculate Au concentrations.

Although the embodiment above has described the case in which a measurement gas is an exhaust gas present in an exhaust pipe of an internal combustion engine such as a diesel engine or a gasoline engine and the concentration of an unburned hydrocarbon gas in the measurement gas is determined, the measurement targets for the gas sensors 100A to 100C are not limited to a hydrocarbon gas. The gas sensors 100A to 100C can measure $NH_3$ and NOx based on the principle of mixed potential, as in the embodiment described above.

EXAMPLE

Sensor elements 101A were produced on three different production conditions, namely, condition A, condition B, and condition C, and the initial characteristics (sensitivity characteristics immediately after the production) of the sensor elements 101A were evaluated. Also, Pt—Au alloy particles 10A included in sensing electrodes 10 were subjected to AES depth profile analysis, and Au concentrations were calculated based on Expression (1).

Specifically, a conductive paste produced by liquid-state Au mixing was used to form the sensing electrode 10 in every sensor element 101A, whereas in condition A, a Au mixing ratio in a raw material was set to 10 wt % and a sheath member S was used to set a Au vapor pressure around the sensing electrode 10 to $10^{-6}$ atm or more in firing. In condition B, a Au mixing ratio in a raw material was set to 10 wt %, and no sheath member S was used in firing. In condition C, a Au mixing ratio in a raw material was set to 5 wt %, and no sheath member S was used in firing. Three samples (condition A: a-1 to a-3, condition B: b-1 to b-3) were produced in each of conditions A and B, and two samples (c-1 and c-2) were produced in condition C.

The conditions of an evaluation gas used to evaluate initial characteristics are as follows, where specifically, HC is $C_2H_4$.

Flow rate: 5 L/min
Pressure: 1 atm
Gas Temperature: 250° C. (sensor drive temperature: 600° C.)
Composition: $O_2$=10%, $H_2O$=5%, HC=200-2000 ppmC, $N_2$=the remainder AES analysis conditions are as follows.
Apparatus: Field Emission Auger Electron Spectrometer (SAM680 from Physical Electronics USA Inc.)
Measurement Condition: Accelerating Voltage of 20 keV
Analysis Area: diameter of approximately 50 nm (spot analysis of the noble metal particle exposed on the surface of the sensing electrode 10)
Sputtering Ion Species: $Ar^+$ (the sputtering depth corrected according to Au standard sample)

Table 1 shows the conditions for producing the sensor elements 101A and the results of the depth profile analysis of Au concentrations. In Table 1, "n/a" indicates that a resultant value is not greater than a detection limit.

TABLE 1

| Conditions | | A | | | B | | | C | |
|---|---|---|---|---|---|---|---|---|---|
| Au concentration (%) | Au mixing ratio in raw material | 10 wt % | | | 10 wt % | | | 5 wt % | |
| | Sheath member in firing | Used | | | Not used | | | Not used | |
| | Sample No. | a-1 | a-2 | a-3 | b-1 | b-2 | b-3 | c-1 | c-2 |
| Analysis depth (nm) | 0 (surface) | 28 | 24 | 30 | 15 | 13 | 14 | 7 | 8 |
| | 0.75 | 15 | 21 | 18 | 7 | 0 | 5 | n/a | n/a |
| | 1.5 | 13 | 15 | 15 | n/a | n/a | n/a | n/a | n/a |
| | 3 | 7 | 4 | n/a | n/a | n/a | n/a | n/a | n/a |
| | 4.5 | n/a | n/a | n/a | n/a | n/a | n/a | n/a | n/a |
| Initial characteristics | | ⊚ | | | ○ | | | X | |
| Durability | | ⊚ | | | X | | | Not evaluated | |

As shown in Table 1, for samples a-1 to a-3 produced in condition A, the Au concentrations in the surfaces of the Pt—Au alloy particles 10A were 24 to 30%, and values of not smaller than 13% were obtained at a depth of 1.5 nm from the surface. However, the Au concentrations at a depth of 3 nm from the surface were not greater than 7%. This confirmed that in the production of the sensing electrode 10 in condition A, a Au enriched region having a Au concentration of 10% or more is formed in the range of at least 1.5 nm in depth from the surface of the Pt—Au alloy particle 10A. The EPMA measurement on the cross-section of the Pt—Au alloy particle 10A, separately performed, confirmed that Au was also present inside the Pt—Au alloy particle 10A, where a resultant value in AES was below the detection limit.

For samples b-1 to b-3 produced in condition B, the Au concentrations in the surfaces of the Pt—Au alloy particles 10A were 13 to 15% and decreased down to 7% or less at a depth of 0.75 nm from the surface, and no Au was detected at a much deeper portion. This confirmed that in the production of the sensing electrode 10 in condition B, a Au enriched region having a Au concentration of 10% or more is formed at least in the surface of the Pt—Au alloy particle 10A.

For samples c-1 and c-2 produced in condition C, however, the Au concentrations were, at most, 8%. Specifically, it was confirmed that no Au enriched region is formed in the production of the sensing electrode 10 in condition C.

The results above indicate that a Au enriched region can be formed at least in the surface of the Pt—Au alloy particle 10A by forming a sensing electrode 10 with a Au mixing ratio of 10 wt % as in conditions A and B. The results also indicate that a Au enriched region can be formed in a range deeper from the surface of the Pt—Au alloy particle 10A by setting a Au vapor pressure around the sensing electrode 10 to $10^{-6}$ atm or more using the sheath member S in firing as in condition A than in the case where no sheath member S was used. More specifically, the results indicate that a Au enriched region can be formed in the range of at least 1.5 nm in depth from the surface of the Pt—Au alloy particle 10A.

Figure 8:
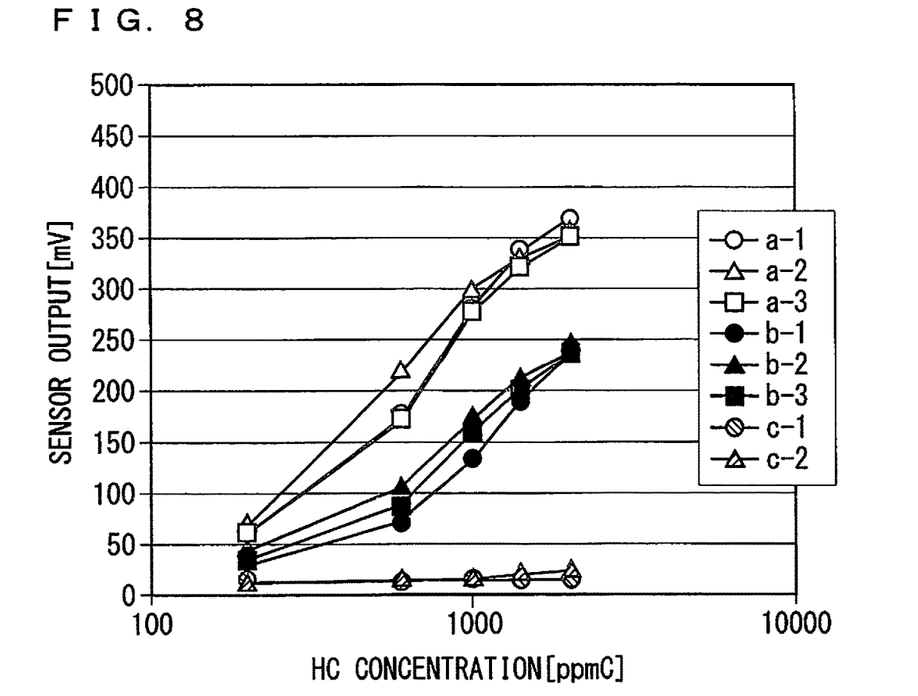
FIG. 8 illustrates initial characteristics of individual samples of an example.

FIG. 8 illustrates the initial characteristics of the respective samples. The initial characteristics are judged, at 1000 ppmC, to be good if sensor outputs of 250 mV or more were obtained, to be permissible if sensor outputs of 100 mV or more and less than 250 mV obtained, and to be inadequate if sensor outputs of less than 100 mV were obtained. As illustrated in FIG. 8, samples a-1 to a-3 produced in condition A resulted in sensor outputs exceeding 250 mV, approximately 280 to 300 mV, and samples b-1 to b-3 produced in condition B resulted in sensor outputs in the neighborhood of 150 mV. In contrast, the sensor outputs of samples c-1 to c-2 produced in condition C were, at most, approximately 20 mV.

Table 1 also shows the evaluations of the initial characteristics for every condition of the sensor element 101A, which are obtained from those results. Specifically, "⊚" (double circle) is placed for condition A in which all the sensor outputs of the produced samples are judged to be good, "○" (circle) is placed for condition B in which the sensor outputs are judged to be permissible, and "×" (christcross) is placed for condition C in which the sensor outputs are judged to be inadequate.

Considering the surface concentrations of the Pt—Au alloy particles 10A as well as the evaluation results of the initial characteristics, it can be said that the formation of a Au enriched region in the surface of the Pt—Au alloy particle 10A is necessary for the sensor element 101A to have such sensitivity characteristics that make the concentration of a measurement gas identifiable at least in its early use.

Subsequently, for sample a-1 in condition A and sample b-1 in condition B, whose initial characteristics were above a permissible level, durability of the sensing electrode 10 was evaluated by the accelerated degradation test. Specifically, the sensor outputs were continuously monitored while the respective samples were placed in the evaluation gas atmosphere in the conditions below. A test time was 13 hours.

Figure 9:
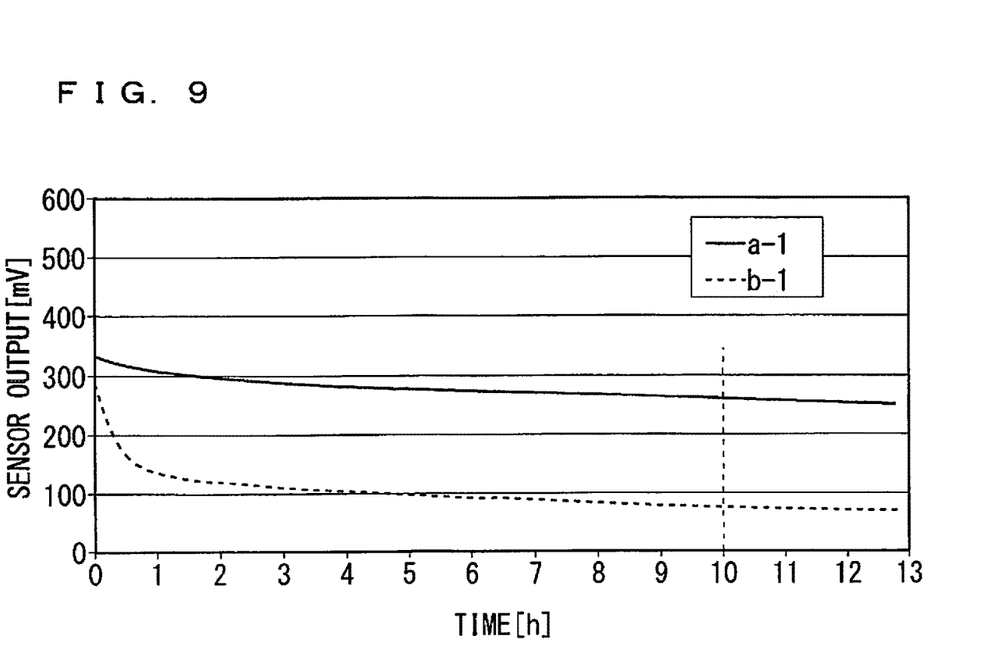
FIG. 9 illustrates results of accelerated degradation tests on sample a-1 and sample b-1.

Flow rate: 0.5 L/min
Pressure: 1 atm
Gas Temperature: 120° C. (sensor drive temperature: 600° C.)
Composition: $O_2$=10%, HC=8000 ppmC, $N_2$=the remainder FIG. 9 illustrates the results of the accelerated degradation test on the respective samples. The durability of the sensing electrode 10 is judged to be good if a ratio of a sensor output after a lapse of 10 hours from the start of the test to a sensor output immediately after the start of the test is 75% or more, and durability is judged to be inadequate if the ratio is less than 75%. In sample a-1 produced in condition A, a sensor output after a lapse of 10 hours from the start of the test was 260 mV, which is a value accounting for 79% of the sensor output after the start of the test, 330 mV. In sample b-1 produced in condition B, a sensor output after a lapse of 10 hours from the start of the test was 75 mV, which is a value accounting for 26% of the sensor output after the start of the test, 286 mV. In other words, compared with sample b-1, sample a-1 had a great initial sensor output value and had small variations in output.

The magnitudes of the sensor outputs differ between FIGS. 8 and 9 because a protective cover to be attached to the outside of the gas sensor was changed to accelerate the degradation of an electrode in the accelerated deterioration test.

Table 1 also shows the evaluations on durability of the sensor element 101A obtained from the results of the accelerated degradation test. Specifically, "⊚" (double circle) is placed in condition A in which durability is judged to be good, and "x" (christcross) is placed in condition B in which durability is judged to be inadequate.

Considering the results of evaluations on durability as well as how a Au enriched region was formed described above, a sensor element 101A including a sensing electrode 10 with excellent durability can be achieved by forming a Au enriched region in the range of at least 1.5 nm in depth from the surface of the Pt—Au alloy particle 10A.

What is claimed is:

1. A mixed-potential gas sensor for measuring a concentration of a predetermined gas component of a measurement gas, the gas sensor comprising:
   a sensor element mainly made of an oxygen-ion conductive solid electrolyte;
   a sensing electrode located on a surface of said sensor element; and
   a reference electrode including a cermet of Pt and an oxygen-ion conductive solid electrolyte,
   wherein
   said sensing electrode includes a cermet comprising a plurality of noble metal particles and oxygen-ion conductive solid electrolyte particles,
   said noble metal particles each comprise an alloy of Pt and Au,
   for at least one of the plurality of noble metal particles, a range of at least 1.5 nm from a surface of each of the at least one of the plurality of noble metal particles is a Au enriched region having a Au concentration of 10% or more, and
   the gas sensor determines the concentration of said predetermined gas component based on a potential difference between said sensing electrode and said reference electrode.

2. The gas sensor according to claim 1, wherein said Au concentration is a value calculated from an expression $$\text{Au concentration (\%)}=100\times\text{Au detection value}/(\text{Au detection value}+\text{Pt detection value})$$

where a Au detection value and a Pt detection value are values in Auger spectrum obtained by performing a measurement on the surface of said at least one of the plurality of noble metal particles by Auger electron spectroscopy.

3. The gas sensor according to claim 2, further comprising an electrode protective layer that is a porous layer covering at least said sensing electrode.

4. The gas sensor according to claim 3, wherein
   said sensor element further includes a reference gas introduction space into which a reference gas is introduced, said reference gas introduction space separated from a space containing said measurement gas, and
   said reference electrode is placed in an atmosphere of said reference gas.

5. The gas sensor according to claim 3, wherein said sensing electrode and said reference electrode are disposed on the surface of said sensor element.

6. The gas sensor according to claim 2, wherein
   said sensor element further includes a reference gas introduction space separate from a space containing said measurement gas, into which a reference gas is introduced, and
   said reference electrode is placed in an atmosphere of said reference gas.

7. The gas sensor according to claim 2, wherein said sensing electrode and said reference electrode are disposed on the surface of said sensor element.

8. The gas sensor according to claim 1, further comprising an electrode protective layer that is a porous layer covering at least said sensing electrode.

9. The gas sensor according to claim 8, wherein
   said sensor element further includes a reference gas introduction space into which a reference gas is introduced, said reference gas introduction space separated from a space containing said measurement gas, and
   said reference electrode is placed in an atmosphere of said reference gas.

10. The gas sensor according to claim 8, wherein said sensing electrode and said reference electrode are disposed on the surface of said sensor element.

11. The gas sensor according to claim 1, wherein
    said sensor element further includes a reference gas introduction space into which a reference gas is introduced, said reference gas introduction space separated from a space containing said measurement gas, and
    said reference electrode is placed in an atmosphere of said reference gas.

12. The gas sensor according to claim 11, wherein
    said sensor element further includes a reference gas introduction layer that is a porous layer in communication with said reference gas introduction space, and
    said reference electrode is covered with said reference gas introduction layer.

13. The gas sensor according to claim 11, wherein said reference electrode is exposed to said reference gas introduction space.

14. The gas sensor according to claim 1, wherein said sensing electrode and said reference electrode are disposed on the surface of said sensor element.

15. The gas sensor according to claim 14, wherein said sensing electrode and said reference electrode are covered with an electrode protective layer.

16. The gas sensor according to claim 1, wherein said predetermined gas component comprises at least one of a hydrocarbon component or a carbon monoxide component.

17. A method for manufacturing a mixed-potential gas sensor for measuring a concentration of a predetermined gas component of a measurement gas, said gas sensor comprising:
    a sensor element mainly made of an oxygen-ion conductive solid electrolyte;
    a sensing electrode located on a surface of said sensor element; and
    a reference electrode including a cermet of Pt and an oxygen-ion conductive solid electrolyte,
    wherein
    said sensing electrode includes a cermet comprising a plurality of noble metal particles and oxygen-ion conductive solid electrolyte particles, said noble metal particles each comprise an alloy of Pt and Au, for at least one of the plurality of noble metal particles, a range of at least 1.5 nm from a surface of each of the at least one of the plurality of noble metal particles is a Au enriched region having a Au concentration of 10% or more, the gas sensor determines the concentration of said predetermined gas component based on a potential difference between said sensing electrode and said reference electrode, said method comprising:
(a) preparing a plurality of green sheets each comprising said solid electrolyte;
(b) applying a conductive paste whose weight ratio of Au to a noble metal component is 10 wt % or more to one of said plurality of green sheets to form a pattern of said sensing electrode;
(c) forming a laminated body of said plurality of green sheets including the green sheet on which the pattern of said sensing electrode has been formed; and
(d) firing said laminated body to integrally fire said sensing electrode with said solid electrolyte, wherein in said step (d), a Au vapor pressure near the pattern of said sensing electrode is set to $10^{-6}$ atm or more when the laminated body is fired.

18. The method according to claim 17, wherein in said step (d), when said laminated body is fired, said laminated body is enclosed by a predetermined member to set a Au vapor pressure near the pattern of said sensing electrode to $10^{-6}$ atm or more.

19. The method according to claim 17, wherein said Au concentration is a value calculated from an expression $$\text{Au concentration (\%)} = 100 \times \text{Au detection value}/(\text{Au detection value} + \text{Pt detection value})$$

where a Au detection value and a Pt detection value are values in Auger spectrum obtained by performing a measurement on the surface of said at least one of the plurality of noble metal particles by Auger electron spectroscopy.

20. The method according to claim 18, wherein said Au concentration is a value calculated from an expression $$\text{Au concentration (\%)} = 100 \times \text{Au detection value}/(\text{Au detection value} + \text{Pt detection value})$$

where a Au detection value and a Pt detection value are values in Auger spectrum obtained by performing a measurement on the surface of said at least one of the plurality of noble metal particles by Auger electron spectroscopy.

* * * * *